US011305501B2

(12) United States Patent
Liu et al.

(10) Patent No.: US 11,305,501 B2
(45) Date of Patent: Apr. 19, 2022

(54) METHODS AND APPARATUS FOR FABRICATING POROUS THREE-DIMENSIONAL TUBULAR SCAFFOLDS

(75) Inventors: Qing Liu, Hillsborough, NJ (US); Zongsen Wang, Princeton, NJ (US); Wing K. Lau, Basking Ridge, NJ (US)

(73) Assignee: BEIJING ADVANCED MEDICAL TECHNOLOGIES, CO., LTD., Beijing (CN)

(*) Notice: Subject to any disclaimer, the term of this patent is extended or adjusted under 35 U.S.C. 154(b) by 766 days.

(21) Appl. No.: 12/823,599

(22) Filed: Jun. 25, 2010

(65) Prior Publication Data
US 2010/0330144 A1 Dec. 30, 2010

Related U.S. Application Data

(60) Provisional application No. 61/220,424, filed on Jun. 25, 2009.

(51) Int. Cl.
| | |
|---|---|
| B29D 23/00 | (2006.01) |
| B33Y 30/00 | (2015.01) |
| B05B 13/04 | (2006.01) |
| B05C 5/02 | (2006.01) |
| B29C 48/395 | (2019.01) |
| B29C 48/365 | (2019.01) |
| B29C 48/485 | (2019.01) |
| B29C 55/22 | (2006.01) |
| A61F 2/07 | (2013.01) |
| B29C 53/60 | (2006.01) |
| B29L 23/00 | (2006.01) |
| A61F 2/91 | (2013.01) |
| B29C 48/05 | (2019.01) |

(52) U.S. Cl.
CPC ........ *B29D 23/001* (2013.01); *B05B 13/0442* (2013.01); *B05C 5/0216* (2013.01); *B29C 48/365* (2019.02); *B29C 48/395* (2019.02); *B29C 48/485* (2019.02); *B33Y 30/00* (2014.12); *A61F 2/07* (2013.01); *A61F 2/91* (2013.01); *B29C 48/05* (2019.02); *B29C 53/60* (2013.01); *B29C 55/22* (2013.01); *B29L 2023/007* (2013.01); *Y10T 428/13* (2015.01); *Y10T 428/1362* (2015.01)

(58) Field of Classification Search
CPC ............. B05B 13/0442; B05C 5/0216; B29C 47/36; B29C 47/38; B29C 47/0014; B29C 53/60; B29C 55/22; B29D 23/001; B33Y 30/00; A61F 2/07; A61F 2/91; B29L 2023/007; Y10T 428/13; Y10T 428/1362
See application file for complete search history.

(56) References Cited

U.S. PATENT DOCUMENTS

| | | | |
|---|---|---|---|
| 4,475,972 A * | 10/1984 | Wong ........................ | A61F 2/06 156/167 |
| 4,665,492 A | 5/1987 | Masters | |
| 4,749,347 A | 6/1988 | Valavaara | |
| 5,121,329 A * | 6/1992 | Crump .......................... | 700/119 |
| 5,134,569 A | 7/1992 | Masters | |
| 5,141,680 A | 8/1992 | Almquist et al. | |
| 5,204,055 A | 4/1993 | Sachs et al. | |
| 5,303,141 A | 4/1994 | Batchelder et al. | |
| 5,340,433 A | 8/1994 | Crump | |
| 5,402,351 A | 3/1995 | Batchelder et al. | |
| 5,501,824 A | 3/1996 | Almquist et al. | |
| 5,503,785 A | 4/1996 | Crump et al. | |
| 5,555,176 A | 9/1996 | Menhennett et al. | |
| 5,569,349 A | 10/1996 | Almquist et al. | |
| 5,645,677 A * | 7/1997 | Cahuzac ............. | B29C 53/8016 156/361 |
| 5,653,925 A | 8/1997 | Batchelder | |
| 5,717,599 A | 2/1998 | Menhennett et al. | |
| 5,738,817 A | 4/1998 | Danforth et al. | |
| 5,764,521 A | 6/1998 | Batchelder et al. | |
| 5,866,058 A | 2/1999 | Batchelder et al. | |
| 5,900,207 A | 5/1999 | Danforth et al. | |
| 5,939,008 A | 8/1999 | Comb et al. | |
| 5,986,561 A | 10/1999 | Batchelder et al. | |
| 6,056,993 A * | 5/2000 | Leidner et al. .............. | 427/2.25 |
| 6,067,480 A | 5/2000 | Stuffle et al. | |
| 6,238,613 B1 | 5/2001 | Batchelder et al. | |
| 6,645,412 B2 | 11/2003 | Priedeman, Jr. | |
| 6,823,230 B1 | 11/2004 | Jamalabad et al. | |
| 7,122,057 B2 | 10/2006 | Beam et al. | |
| 7,236,166 B2 | 6/2007 | Zinniel et al. | |
| 7,297,304 B2 | 11/2007 | Swanson et al. | |
| 7,374,712 B2 | 5/2008 | Swanson et al. | |
| 7,403,833 B2 | 7/2008 | Heide et al. | |
| 7,445,441 B2 | 11/2008 | West et al. | |
| 7,622,299 B2 | 11/2009 | Sanders et al. | |
| 7,897,074 B2 | 3/2011 | Batchelder et al. | |
| 7,981,353 B2 * | 7/2011 | Mitchell ................ | A61L 27/14 264/465 |
| 8,221,669 B2 | 7/2012 | Batchelder et al. | |
| 8,439,665 B2 | 5/2013 | Batchelder et al. | |
| 8,463,418 B2 | 6/2013 | Liu et al. | |

(Continued)

FOREIGN PATENT DOCUMENTS

| | | | | |
|---|---|---|---|---|
| WO | WO2009026200 | * | 2/2009 | ............... G06G 7/48 |
| WO | WO-2009026200 A1 | * | 2/2009 | ......... B29C 47/0866 |

OTHER PUBLICATIONS

Leidner J of Biochem. Mat. erials Res. 1983, p. 229.*
Written Opinion and International Search Report for International Patent Application No. PCT/US2010/039993 dated Sep. 20, 2010.

*Primary Examiner* — Matthew P Coughlin
*Assistant Examiner* — Thurman Wheeler
(74) *Attorney, Agent, or Firm* — Daniel J. Chalker; Edwin S. Flores; Chalker Flores, LLP

(57) ABSTRACT

Disclosed herein are three-dimensional porous tubular scaffolds for cardiovascular, periphery vascular, nerve conduit, intestines, bile conduct, urinary tract, and bone repair/reconstruction applications, and methods and apparatus for making the same.

17 Claims, 6 Drawing Sheets

(56) References Cited

U.S. PATENT DOCUMENTS

| | | |
|---|---|---|
| 2002/0090725 A1* | 7/2002 | Simpson et al. ............... 435/402 |
| 2002/0113331 A1 | 8/2002 | Zhang et al. |
| 2006/0175727 A1* | 8/2006 | Fierens .................... A61F 2/91 |
| | | 264/172.19 |
| 2007/0009570 A1* | 1/2007 | Kim et al. .................... 424/423 |
| 2007/0027535 A1* | 2/2007 | Purdy, Jr. ................ A61L 27/18 |
| | | 623/2.18 |
| 2007/0269481 A1* | 11/2007 | Li .......................... A61L 27/18 |
| | | 424/423 |
| 2008/0194010 A1 | 8/2008 | Liu |
| 2008/0300668 A1* | 12/2008 | Bonsignore ............... A61F 2/91 |
| | | 623/1.15 |
| 2009/0035449 A1 | 2/2009 | Chen et al. |
| 2009/0238853 A1 | 9/2009 | Liu et al. |
| 2011/0196660 A1 | 8/2011 | Liu et al. |

* cited by examiner

METHODS AND APPARATUS FOR FABRICATING POROUS THREE-DIMENSIONAL TUBULAR SCAFFOLDS

RELATED APPLICATIONS

This application claims priority to U.S. Provisional Application No. 61/220,424, filed Jun. 25, 2009, the content of which is hereby incorporated by reference in its entirety.

BACKGROUND OF THE INVENTION

Regeneration of cellular tissue and organs is a rapidly growing field. Obstacles commonly found with conventional transplantation, such as donor tissue/organ shortage and host rejection, may be overcome by enabling the host to utilize his or her own cells to regenerate cellular tissue, repair a damaged nerve or blood vessel, etc.

One important approach towards creating engineered tissue is Tissue Engineering, which uses a combination of a three-dimensional (3D) scaffold, progenitor cells and biological factors to "grow" a living tissue or organ. A 3D scaffold provides a structure for the cells to adhere to during their regeneration process, thereby guiding the cells into the size and shape of the desired structure. In this tissue regeneration process, the 3D scaffolds must allow cells to readily to attach, rapidly multiply and form new tissue. In the orchestrated process of tissue morphogenesis, cells are significantly influenced by both the micro-architecture of 3D scaffolds and surface biochemical properties for their adhesion, proliferation, migration and differentiation. Therefore, 3D scaffolds should be designed with a preferred biological property and internal architecture in mind, wherein porosity and material connectivity provide the required structural integrity, mass transport and comprehensive micro-environment for cell and tissue growth. In addition, cell survival and proliferation within the 3D scaffold require access to oxygen and vital molecules. The delivery of vital molecules into the 3D scaffold is governed by scaffold-designed structural and topological configuration defined by a few key design parameters, such as, porosity, pore interconnectivity, tortuosity, scaffold material permeability and diffusivity.

The mechanical property of the 3D scaffolds also is an very important feature. The mechanical properties of the 3D scaffolds can be designed to meet the application requirement by designing the porous structure or architecture of the scaffolds so that the 3D scaffolds can be expandable, stretchable, or bendable. Some of the applications will need the cell seeded 3D scaffold to be cultured under cyclic loading to mimic the in vivo dynamic tissue growth environment. Some 3D scaffolds will also need to be foldable or compressed to make them easier for delivery. Once these folded scaffolds are delivered to the sites, they can be unfolded or expanded to perform their desired function.

For example a vascular stent must be expandable and stretchable and strong enough to keep the blood vessel open to allow blood to flow through, and thus requires a scaffold to have a design structure to allow for compressing, expanding and bending. The mechanical properties of the stent can further be adjusted by using materials with different mechanical properties.

Human tissue and organ have various sizes and shapes. Many tissue or organs have distinct tubular structures, such as blood vessels, the esophagus, intestines, the bile conduct, urinary tract, etc. When blood vessels are damaged and need to be regenerated, a three-dimensional tubular scaffold is needed for blood vessel regeneration. The scaffolds provide the cells with an exogenous skeleton for the cells to adhere and grow. Therefore, it is important to have a 3D scaffold manufacturing method to produce scaffolds which match the size and shape of the targeted tubular tissue and organ.

A tubular structure implant is also needed when treating some vascular diseases. For example, a 3D scaffold in the form of a vascular stent can be used to keep the clogged blood vessel open. Although metallic stents are currently widely used clinically, biodegradable polymer stents are under extensive research and development. The greatest advantage of biodegradable stent is that the stent will disappear after a period of time when there is no longer a need to have it in place.

Scaffolds may be manufactured by Rapid Prototyping (RP), a technology that produces models and prototype parts from 3D computer-aided design (CAD) model data and model data created from 3D object digitizing systems. Rapid prototyping is a material addition process in which material is added or deposited at desired location to form the object. Rapid prototyping technologies has also been explored for the development of manufacturing approaches to create surgical implant models for orthopedic and craniofacial surgical procedures. RP systems provide possibilities in fabricating porous 3D object with well controlled channels or pores. However, the current RP systems have only three axis (XYZ) and are not efficient systems for fabricating tubular porous structures. When fabricating tubular porous structures, the current RP systems often need to use a supporting material which will have to be removed after fabrication.

In contrast to the RP of material addition process, there is a way of fabricating porous polymer tubing or a stent using a material reduction process, that is to use a laser tubular micromachining or a laser cutting/removal system that is similar to the fabrication method of a metal vascular stent. In this method, a polymer tube is produced first, and followed by selected removal of polymer in certain areas, according to the porous pattern design, using a laser beam. However, in this fabrication method, a polymer tube has to be made first, followed by laser cutting. Overall, this is a time consuming two-step process. Also, most of the polymer material is removed or wasted, particularly in the case of fabrication of a highly porous polymer stent. This fabrication process can be expensive as medical grade polymer materials are typically expensive. Further, the removal or the evaporation of the polymer by laser beam heating causes toxic gas emission, resulting in air pollution.

Therefore, there is a need to have a one step process or a system which can directly produce porous tubular scaffolds from raw polymer materials based on a CAD design, which will overcome the drawbacks of a laser cutting system, such as wasting of materials, time consuming and air polluting, as well as being able to overcome the drawbacks of a RP system, in which a supporting material has to be used and removed after finishing the fabrication process.

The inventors of the present application have achieved this goal with a 4 axis RP system.

SUMMARY OF THE INVENTION

It is therefore an object of the present invention to provide methods to fabricate porous polymeric three-dimensional (3D) tubular scaffolds whereby the porosity, pore size, structure, and mechanical properties can be easily controlled or manipulated.

It is a further object to the present invention to provide a 4 axis RP system in which the 4th axis is a computer controlled rotation shaft added to an xyz position system. In preferred embodiments, the 4 axis RP system also has a material delivery system that directly deposits polymer material in a hot melt filament form or a viscous solution filament form. The deposited filament adheres to the surface of the rotation shaft or bonds to previously extruded filaments that are already attached to the rotation shaft. In addition, preferred embodiments allow for the fiber diameter to be changed by either varying the rotation speed of the 4th axis where the polymer filament is attached, or by varying the XY axis traveling speed, similar to a hot melt drawing process. This system is particularly suitable for making 3D tubular scaffolds with complicated micro-porous structures.

Thus, in certain embodiments, the present invention is directed to an apparatus for manufacturing a 3D tubular scaffold comprising: (i) a three-axis XYZ system connected to a base; (ii) a dispensing system connected to the XYZ system; (iii) a nozzle connected to the dispensing system; and (iv) a fourth axis system comprising a rotary rod or shaft connected to the base under the nozzle, wherein either the rotary rod, the nozzle or both are capable of moving along a longitudinal axis.

In other embodiment, the present invention is directed to a method of making a 3D tubular scaffold comprising: (i) adding a polymer into the apparatus described herein; and (ii) dispensing the polymer onto a rotary rod.

In further embodiment, the present invention is directed to a 3D tubular scaffold comprising struts and/or fibers joined in a porous three-dimensional pattern, the scaffold having an average pore size from about 1 to about 10000 microns.

In further embodiment, the present invention is directed to a special tubular scaffold called stents which are comprising struts and/or fibers joined in a pre-designed three-dimensional pattern.

DETAILED DESCRIPTION

Figure 1A:
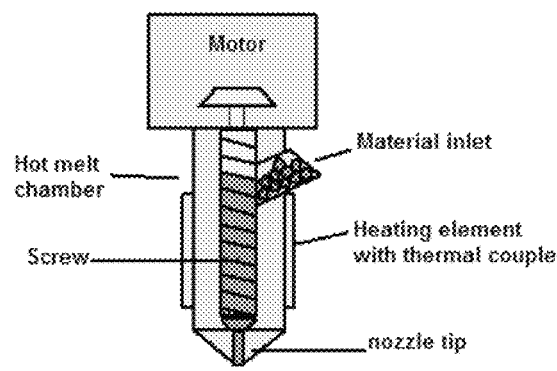
FIG. 1a depicts a micro single screw extruder in certain embodiments of the apparatus of the present invention.
Figure 1B:
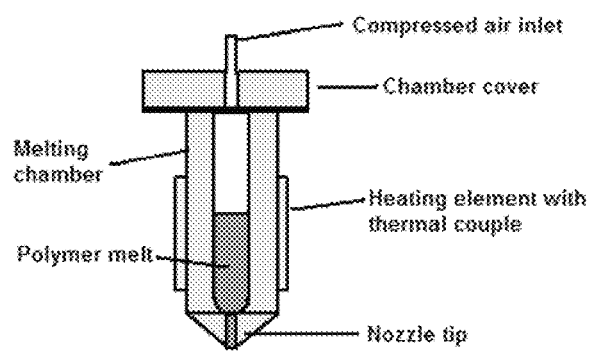
FIG. 1b depicts a hot melt chamber which uses compressed air for extrusion of polymer in certain embodiments of the apparatus of the present invention.

In the 4 axis RP system of the present invention, the $4^{th}$ axis is a computer controlled rotation shaft added to an xyz position system. The 4 axis RP system also has a material delivery system that directly deposits polymer material in a hot melt filament form or a viscous solution filament form. The deposited filament adheres to the surface of the rotation shaft or bonds to previously extruded filaments that already attached to the rotation shaft, therefore eliminating the need to use glue or controlled heating, as previously described in, e.g. US patent application (US 20030211130A1 by Sanders et al). In addition, the fiber diameter can be changed by either varying the rotation speed of the 4th axis where the polymer filament is attached, or by varying the XY axis traveling speed, similar to a hot melt drawing process. This system is particularly suitable for making 3D tubular scaffolds with complicated micro-porous structures.

3D tubular scaffolds made by the 4 axis RP system provides an internal and external space for cellular interactions. The 3D tubular scaffold is composed of polymer fibers which are joined together in a pre-design fashion or pattern. Such a configuration allows the tubular scaffold to have 100% pore interconnection. In addition to the 3D tubular scaffold and 4 axis RP system, the present invention is also directed to methods of manufacturing the 3D tubular scaffold and applications for the 3D tubular scaffold.

3D Tubular Scaffolds

The 3D tubular scaffold of the present invention may be configured in any size to accomplish the particular purpose at hand, e.g., size suitable for use in vasculogenesis, osteogenesis, vascular stents, etc.

The 3D tubular scaffolds can be single layered or multi-layered.

The fibers or the struts of the 3D tubular scaffolds may be joined together in a pre-designed fashion or pattern. For example, the fibers may be joined together in a perpendicular angle)(90°), an acute angle (less than 90°) or at an obtuse angle (more than 90°), or a combination thereof. Additionally, the fibers of the 3D tubular scaffolds may have constant diameters or different diameters. In preferred embodiments, the diameter of the polymer fibers of the 3D tubular scaffolds are from about 50 nm to 2 mm, more preferably from 100 μm to 1000 μm.

The cross sections of the struts and/or fibers may be a circle, triangle, square, rectangle, star, or irregular shape.

The pores of the 3D tubular scaffolds may be a constant size and/or dimension, a variable size and/or dimension or a combination thereof. For example, pores may be a constant size and/or dimension within each layer, but differ from the pore size and/or dimension on different layers. In preferred embodiments, the mean pore size of the 3D tubular scaffolds are from having an average pore size of from about 15 microns to about 1000 microns, from about 25 microns to about 500 microns, or from about 50 microns to about 100 microns. In yet other embodiments, a dense layer may be developed without pores. The 3D tubular scaffolds may have a pore distribution of 0%, greater than about 50%, greater than about 80% or greater than about 95%.

The surface area, porosity and pore size of the 3D tubular scaffolds are determined by the design of the constructs, including the size and geometry of the fibers, number of the fibers in each unit volume and the construction pattern of the fibers in the 3D tubular scaffold. In preferred embodiments, these factors are further controlled by the mobility of certain aspects of the manufacturing apparatus described herein, namely the rotary rod and/or the nozzle.

The 3D tubular scaffolds of the present invention may be made of non-biodegradable polymer, biodegradable polymer, or a combination thereof.

Non-biodegradable polymers for use in the present invention include, for example, non-degradable synthetic polymers, e.g., polystyrene, polyethylene, polypropylene, polycarbonate, polyethylene terephthalate, polyamide, polyvinyle chloride, etc. and mixtures thereof.

Biodegradable polymers for use in the present invention include, for example, polylactic acid (PLA), polyglycolic acid (PGA), polycaprolactone (PCL), polyanhydrides, poly (β-hydroxybutyrate), polydioxanone, poly(DTH iminocarbonate), polypropylene fumarate, etc. copolymers thereof and mixtures thereof.

In certain embodiments, the 3D tubular scaffolds incorporate one or more biomolecules, e.g., by being coated onto the 3D tubular scaffolds, by being extruded together with the polymer when manufacturing the tubular scaffold, or be intermixing the biomolecules with the polymers prior to manufacture. A biomolecule can be a protein, peptide, glycoaminoglycan, a naturally occurring compound or polymer, a therapeutic agent or a combination thereof. Examples of naturally occurring compound or polymer are collagen, laminin, or fibronectin. Therapeutic agents include but are not limited to, antibiotics, hormones, growth factors, anti-tumor agents, anti-fungal agents, anti-viral agents, pain medications, anti-histamines, anti-inflammatory agents, anti-infective, wound healing agents, anti-proliferative agent, wound sealants, cellular attractants, cytokines and the like. A therapeutic agent is anything that when applied to cell would benefit human health.

In certain embodiments, the 3D tubular scaffolds incorporate antibiotics. Antibiotics are chemotherapeutic agents that inhibit or abolish the growth of micro-organisms, such as bacteria, fungi, or protozoans. Examples of common antibiotics are penicillin and streptomycin. Other known antibiotics are amikacin, gentamicin, kanamycin, neomycin, netilmicin, tobramycin, paromomycin, geldanamycin, herbimycin, loracarbef, ertapenem, doripenem, imipenem/cilastatin, meropenem, cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefdinir, cefepime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, prontosil, sulfacetamide, slfamethizole, slfanilimide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin or rifampicin and tinidazole.

In certain embodiments, the 3D tubular scaffolds incorporate hormones. A hormone is a chemical messenger that carries a signal from one cell (or group of cells) to another via the blood. Examples of hormones are melatonin, serotonin, thyroxine, triiodothyronine, epinephrine, norepinephrine, dopamine, antimullerian hormone, adiponectin, adrenocorticotropic hormone, angiotensinogen and angiotensin, antidiuretic hormone, atrial-natriuretic peptide, calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, secretin, somatostatin, thrombopoietin, thyroid-stimulating hormone, thyrotropin-releasing hormone, cortisol, aldosterone, testosterone, dehydroepiandrosterone, androstenedione, dihydrotestosterone, estradiol, estrone, estriol, progesterone, calcitriol, calcidiol, prostaglandins, leukotrienes, prostacyclin, thromboxane, prolactin releasing hormone, lipotropin, brain natriuretic peptide, neuropeptide Y, histamine, endothelin, pancreatic polypeptide, renin, and enkephalin, In certain embodiments, the 3D tubular scaffolds incorporate growth factors. Growth factor refers to a naturally occurring protein capable of stimulating cellular proliferation and cellular differentiation. Examples are transforming growth factor beta (TGF-β), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF or FGF-2), epidermal growth factor (EGF), and hepatocyte growth factor (HGF).

In certain embodiments, the 3D tubular scaffolds incorporate antitumors. Antitumors or antineoplastics are drugs that inhibit and combat the development of tumors. Examples are actinomycin (e.g., actinomycin-D), anthracyclines (e.g., doxorubicin, daunorubicin, epirubicin), bleomycin, plicamycin, Paclitaxel and mitomycin.

In certain embodiments, the 3D tubular scaffolds incorporate anti-fungal agents. An anti-fungal agent is medication used to treat fungal infections. Examples are natamycin, rimocidin, filipin, nystatin, amphotericin B, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, terbinafine, amorolfine, naftifine, butenafine, anidulafungin, caspofungin, micafungin, benzoic acid, ciclopirox, flucytosine, griseofulvin, gentian violet, haloprogin, tolnaftate, undecylenic acid, tea tree oil, citronella oil, lemon grass, orange oil, palmarosa oil, patchouli, lemon myrtle, neem seed oil, coconut oil, zinc, and selenium.

In certain embodiments, the 3D tubular scaffolds incorporate antiviral agents. Antiviral agents are a class of medication used specifically for treating viral infections. Examples are abacavir, aciclovir, acyclovir, adefovir, amantadine, amprenavir, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors (fusion inhibitor), famciclovir, fomivirsen, fosamprenavir, foscarnet, fosfonet; ganciclovir, gardasil, ibacitabine, immunovir, idoxuridine, imiquimod, indinavir, inosine, integrase inhibitor, interferon type III, interferon type II, interferon type I, lamivudine, lopinavir, loviride, MK-0518 (raltegravir), maraviroc, moroxydine, nelfinavir, nevirapine, nexavir, nucleoside analogues, oseltamivir, penciclovir, peramivir, pleconaril, podophyllotoxin, protease inhibitor (pharmacology), reverse transcriptase inhibitor, ribavirin, rimantadine, ritonavir, saquinavir, stavudine, synergistic enhancer (antiretroviral), tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In certain embodiments, the 3D tubular scaffolds incorporate pain medications. Pain medications or analgesics (colloquially known as a painkiller) are members of the diverse group of drugs used to relieve pain. Examples are paracetamoUacetaminophen, nonsteroidal anti-inflammatory drugs (NSAIDs), COX-2 inhibitors (e.g., rofecoxib and celecoxib), morphine, codeine, oxycodone, hydrocodone, diamorphine, pethidine, tramadol, buprenorphine, tricyclic antidepressants (e.g., amitriptyline), carbamazepine, gabapentin and pregabalin.

In certain embodiments, the 3D tubular scaffolds incorporate antihistamines. An antihistamine is a histamine antagonist that serves to reduce or eliminate effects mediated by histamine, an endogenous chemical mediator released during allergic reactions. Examples are H1 antihistamine, aceprometazine, alimemazine, astemizole, azatadine, azelastine, benadryl, brompheniramine, chlorcyclizine, chloropyramine, chlorphenamine, phenylpropanolamine, cinnarizine, clemastine, cyclizine, cyproheptadine, dexbrompheniramine, dexchlorpheniramine, diphenhydramine, doxylamine, ebastine, emedastine, epinastine, fexofenadine, histamine antagonist (e.g., cimetidine, ranitidine, and famotidine; ABT-239, thioperamide, clobenpropit, impromidine, thioperamide, cromoglicate, nedocromil), hydroxyzine, ketotifen, levocabastine, mebhydrolin, mepyramine, mthapyrilene, methdilazine, olopatadine, pheniramine, phenyltoloxamine, resporal, semprex-D, sominex, talastine, terfenadine, and triprolidine.

In certain embodiments, the 3D tubular scaffolds incorporate anti-inflammatory agents. Anti-inflammatory agent refers to a substance that reduces inflammation. Examples are corticosteroids, ibuprofen, diclofenac and naproxen, helenalin, salicylic acid, capsaicin, and omega-3 fatty acids.

In certain embodiments, the 3D tubular scaffolds incorporate anti-infective agents. Anti-infective agent is any agent capable of preventing or counteracting infection. It could be divided into several groups. Anthelminthics is one group of anti-infective agents comprising of albendazole, levamisole, mebendazole, niclosamide, praziquantel, and pyrantel. Another group is antifilarials, such as diethylcarbamazine, ivermectin, suramin sodium, antischistosomals and antitrematode medicine, oxamniquine, praziquantel, and triclabendazole. Another group is the antibacterials, which can be further subdivided. The beta lactam medicines are amoxicillin, ampicillin, benzathine benzylpenicillin, benzylpenicillin, cefazolin, cefixime, ceftazidime, ceftriaxone, cloxacillin, co-amoxiclav, imipenem/cilastatin, phenoxymethylpenicillin, and procaine benzylpenicillin. Other antibacterials are azithromycin, chloramphenicol, ciprofloxacin, clindamycin, co-trimoxazole, doxycycline, erythromycin, gentamicin, metronidazole, nitrofurantoin, spectinomycin, sulfadiazine, trimethoprim, and vancomycin. Examples of antileprosy medicines are clofazimine, dapsone, and rifampicin. Examples of antituberculosis medicines are amikacin, p-aminosalicylic acid, capreomycin, cycloserine, ethambutol, ethionamide, isoniazid, kanamycin, ofloxacin, pyrazinamide, rifampicin, and streptomycin. Examples of antifungal medicines are amphotericin B, clotrimazole, fluconazole, flucytosine, griseofulvin, nnystatin, potassium iodide. Antiviral agents are also anti-infective agents. An example of a antiherpes medicine is acyclovir. Examples of antiretrovirals are nucleoside/nucleotide reverse transcriptase inhibitors. Other examples are abacavir, didanosine, emtricitabine, lamivudine, stavudine, tenofovir disoproxil fumarate, zidovudine, non-nucleoside reverse transcriptase inhibitors, efavirenz, nevirapine, protease inhibitors, indinavir, lopinavir+ritonavir, nelfinavir, ritonavir, saquinavir and ribavirin. Examples of antiprotozoal medicines are antiamoebic and antigiardiasis medicines such as diloxanide, metronidazole; antileishmaniasis medicines such as amphotericin B, meglumine antimoniate, pentamidine; antimalarial medicines, such as amodiaquine, artemether, artemether+lumefantrine, artesunate, chloroquine, doxycycline, mefloquine, primaquine, quinine, sulfadoxine+pyrimethamine, chloroquine, and proguanil. Antipneumocytosis and antioxoplasmosis medicines are pentamindine, pyrimethamine, sulfamethoxazole+trimethoprim. Antitrypanosomal medicines are eflornithine, melarsoprol, pentamidine, suramin sodium, benznidazole, and nifurtimox. Antimigraine medicines, acetylsalicylic acid, paracetamol, and propranolol.

In certain embodiments, the 3D tubular scaffolds incorporate wound healing agents. Wound healing agents facilitate the body's natural process of regenerating dermal and epidermal tissue. Examples are fibrin, fibronectin, collagen, serotonin, bradykinin, prostaglandins, prostacyclins, thromboxane, histamine, neuropeptides, kinins, collagenases, plasminogen activator, zinc-dependent metalloproteinases, lactic acid, glycosaminoglycans, proteoglycans, glycoproteins, glycosaminoglycans (GAGs), elastin, growth factors (PDGF, TGF-$\beta$), nitric oxide, and matrix metalloproteinases, Examples of wound sealants are platelet gel and fibrin.

In certain embodiments, the 3D tubular scaffolds incorporate anti-proliferative agents. Anti-proliferative agents prevent tissue from growth, such as to prevent restenosis (recurrent narrowing) of coronary, scar tissue formation, etc. an example of anti-proliferative agent is Paclitaxel. Applying a paclitaxel coating in a coronary stent limits restenosis or the growth of neointima (scar tissue).

In certain embodiments, the 3D tubular scaffolds incorporate cellular attractants. Cellular attractants or chemotaxic agents are chemicals or molecules in the environment that are sensed by bodily cells, bacteria, and other single-cell or multicellular organisms affecting their movements. Examples are amino acids, formyl peptides [e.g., N-formylmethionyl-leucyl-phenylalanine (fMLF or fMLP in references], complement 3a (C3a) and complement 5a (C5a), chemokines (e.g., IL-8); leukotrienes [e.g., leukotriene B4 (LTB4)].

In certain embodiments, the 3D tubular scaffolds incorporate cytokines. Cytokines are group of proteins and peptides that are signaling compounds produced by animal cells to communicate with one another. Cytokines can be divided into several families. Examples are the four alpha-helix bundle family with three subfamilies: the IL-2 subfamily [e.g., erythropoietin (EPO) and thrombopoietin (THPO)], the interferon (IFN) subfamily, the IL-10 subfamily. Other examples are the IL-1 family (e.g., IL-1 and IL-18), the IL-17 family, chemokines, immunoglobulin (Ig) superfamily, haemopoietic growth factor (type I) family, Interferon (type 2) family, tumor necrosis factors (TNF) (type 3) family, seven transmembrane helix family, and transforming growth factor beta superfamily.

In certain embodiments, the surface or partial surface of the 3D tubular scaffolds can be further treated by a physiochemical mean, a chemical mean, a coating mean, or a combination thereof to improve cellular attachment.

In certain embodiments, the surface of the 3D tubular scaffold can be further treated with surface modification techniques pertaining to physiochemical means known in the art to improve the surface property of the tubular scaffold for better cellular attachment, by treatment with, e.g., plasma or glow discharge.

Additionally, the surface of the 3D s tubular scaffolds can be further surface treated by chemical means, particularly with acids or bases. In a specific embodiment, the tubular scaffold is treated with $H_2SO_4$, $HNO_3$, HCl, $H_3PO_4$, $H_2CrO_4$, or a combination thereof. In a specific embodiment, the tubular scaffold is treated with NaOH, KOH, $Ba(OH)_2$, CsOH, $Sr(OH)_2$, $Ca(OH)_2$, LiOH, RbOH, or a combination thereof.

The surface of the 3D tubular scaffolds may also be treated by coating means, in which a substance is applied on the surface that is different from the material of the struts and/or fibers. The substance can be covalently bonded or physically absorbed to the surface of the struts and/or fibers. Alternatively, the substance can be bonded to the surface of the construct through hydrogen bonding, ionic bonding, Van der Waals force or a combination thereof. To increase the stability of the biological molecular coating, the coating can be crosslinked using various crosslinking technologies, such as chemical crosslinking, radiation, thermal treatment, or a combination thereof, etc. Further, the crosslinking can take place in a vacuum at an elevated temperature above room temperature. The radiation used for crosslinking can be e-beam radiation, gamma radiation, ultraviolet radiation, or a combination thereof.

The coating substance can be a protein, peptide, glycoaminoglycan, a naturally occurring substance, an inorganic substance, a therapeutic agent, or a combination thereof.

The surface of the 3D tubular scaffolds can be further coated with biological molecules or naturally occurring compound or polymer, such as, but not limited to, collagen (type I, II, III, IV, V, IV, etc), fibronectin, laminin, or other extracellular matrix molecules. Examples of extracellular matrix molecules are heparan sulfate, chondroitin sulfate, keratan sulfates, hyaluronic acid, elastin, hemicellulose, pectin, and extensin. The biological molecules are either covalently bonded to the surface, or physically absorbed to the surface of the tubular scaffolds.

The surface of the 3D tubular scaffolds can be further surface coated with a synthetic polymer, such as, polyvinyl alcohol, polyethylene glycol, polyvinyl polypyrrolidone, poly(L-lactide), polylysine, etc.

The surface of the 3D tubular scaffolds can also be coated with organic substance, such as gelatin, chitosan, polyacrylic acid, polyethylene glycol, polyvinyl alcohol, polyvinylpyrrilidone or a combination thereof.

Alternatively, the 3D s tubular scaffolds may be coated with an inorganic material, such as calcium phosphate, $TiO_2$, $Al_2O_3$, or a combination thereof.

In a specific embodiment, the 3D tubular scaffolds are coated with a composite coating of two or more organic materials, such as, gelatin and chitosan, polyacrylic acid and polyethylene glycol, polyvinyl alcohol and polyvinylpyrrilidone, etc.

The 3D tubular scaffolds may also be coated with a composite of inorganic materials, such as calcium phosphate and $TiO_2$, calcium phosphate and $Al_2O_3$, etc.

The 3D tubular scaffolds may also be coated with a composite coating of a combination of inorganic and organic materials, such as, calcium phosphate/collagen, calcium phosphate/gelatin, calcium phosphate/polyethylene glycol, etc.

The 3D tubular scaffolds of the present invention may also be used together with fabrics. The fabrics can be attached either to the outer surface or the inner surface or to both surfaces of the tubular scaffolds.

The fabrics for attaching to 3D tubular scaffolds can be either woven or non-woven fabrics or both.

The fabrics can be prefabricated or directly fabricated on the outer surface of the 3D tubular scaffolds. The direct fabrication method will included, but not limit to, an electrospinning fabrication method in which the rotation shaft with the 3D scaffolds still on serves as the fiber collector.

The Apparatus and Methods of Manufacture of a 3D Tubular Scaffold

Figure 2:
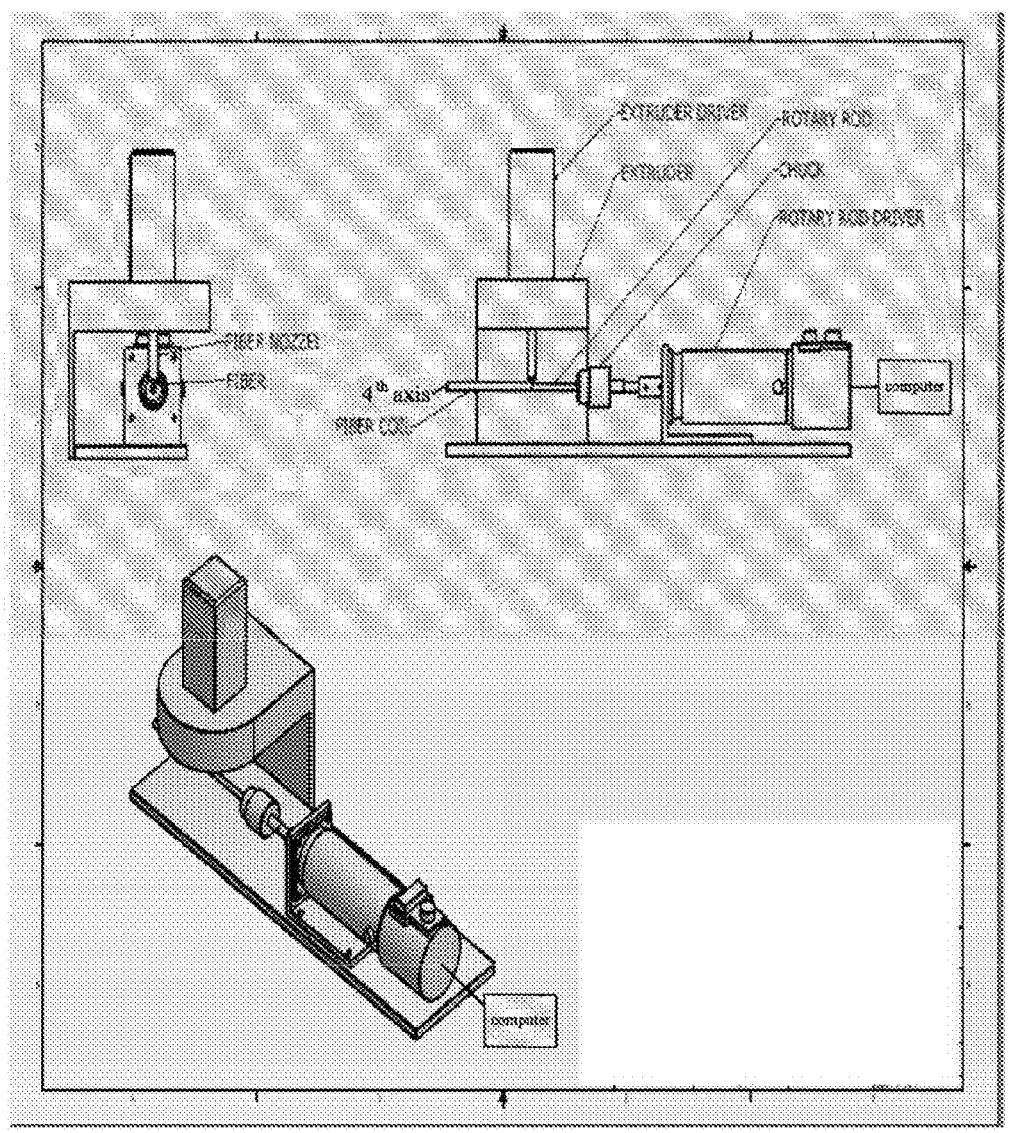
FIG. 2 depicts an embodiment of the apparatus used to manufacture 3D tubular scaffolds of the present invention.
Figure 3A:
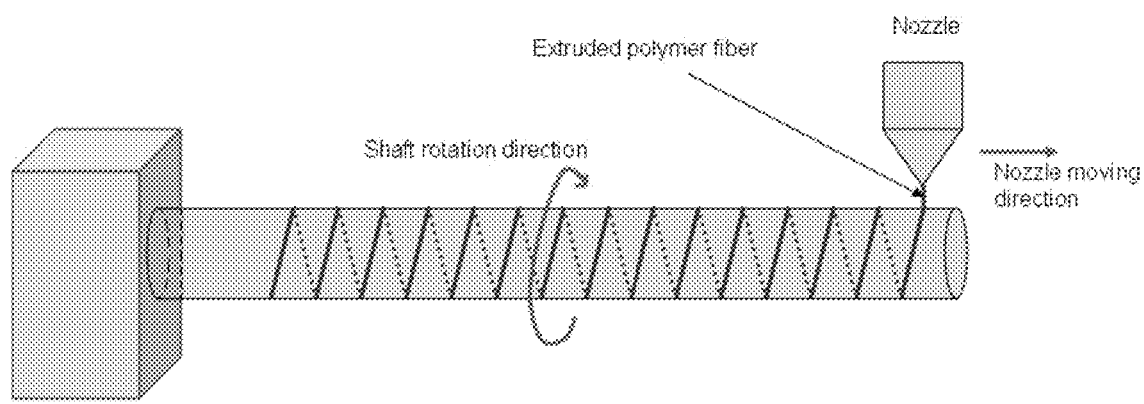
FIGS. 3(a) and (b) depict an embodiment of the apparatus of the present invention, wherein the nozzle moves in a longitudinal direction along the rotating shaft.
Figure 3:
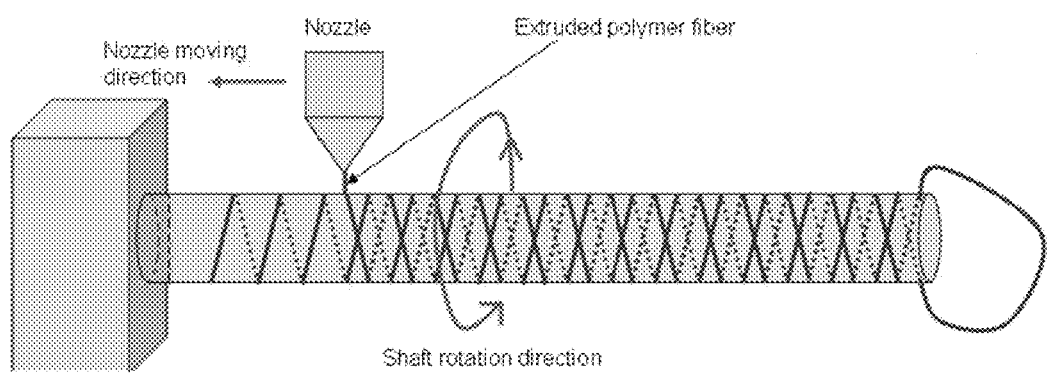
Figure 4:
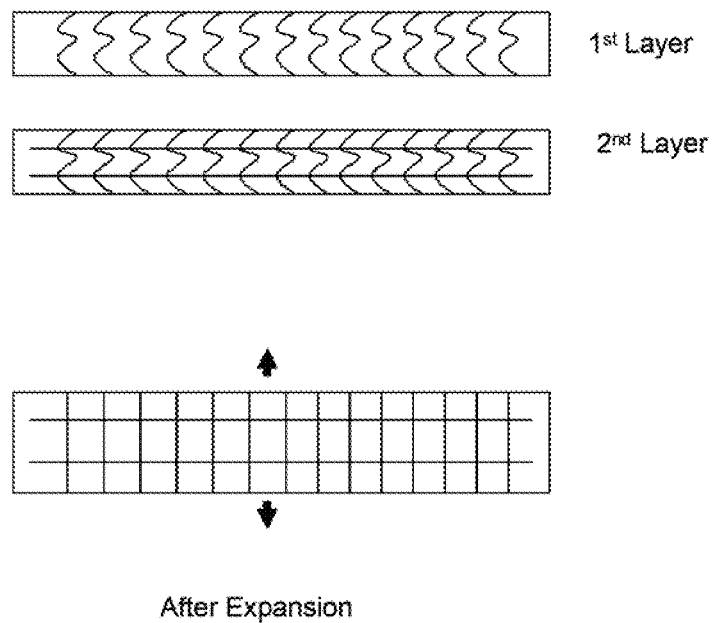
FIG. 4 depicts polymers of an embodiment of the 3D tubular scaffold of the present invention after expansion.
Figure 5:
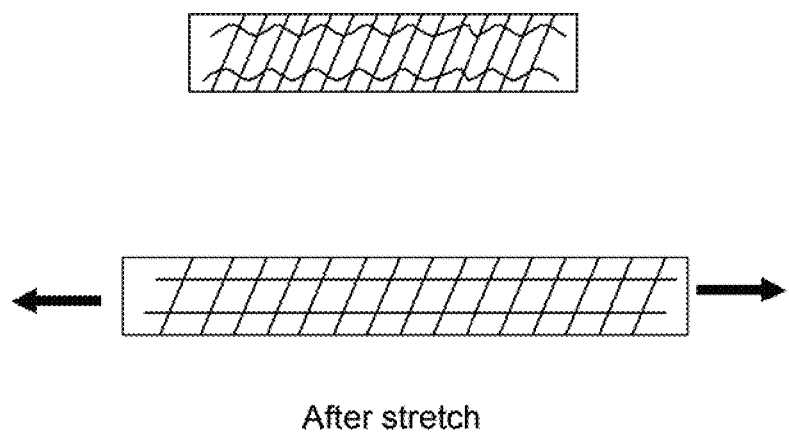
FIG. 5 depicts polymers of an embodiment of the 3D tubular scaffold of the present invention after stretching.
Figure 6:
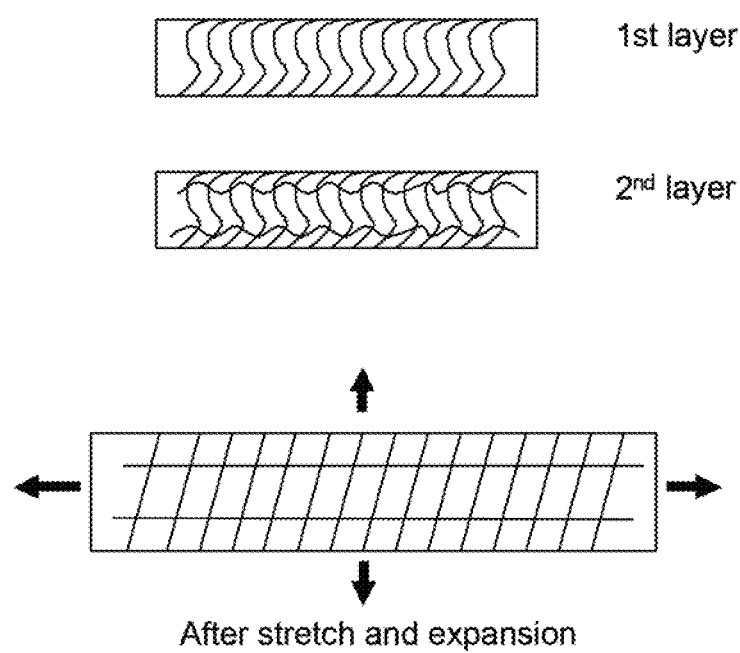
FIG. 6 depicts polymers of an embodiment of the 3D tubular scaffold of the present invention after a combination of expansion and stretching.
Figure 7:
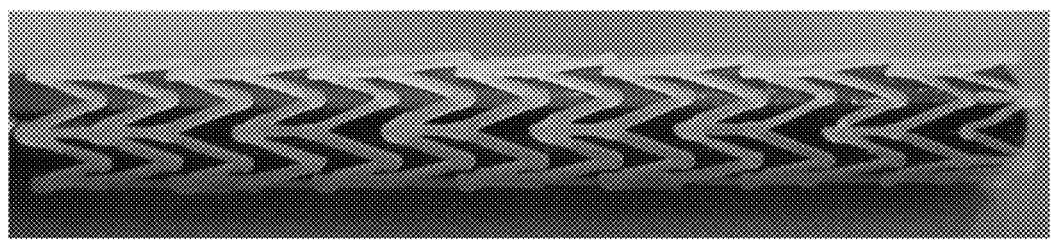
FIG. 7 depicts an embodiment of the 3D tubular scaffold of the present invention illustrating an expandable polymer stent.
Figure 8:
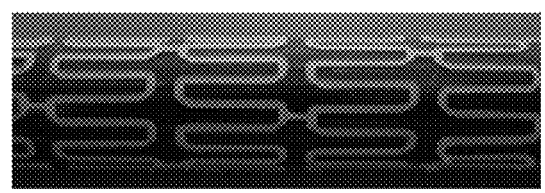
FIG. 8 depicts another example of a polymer stent.

As illustrated in FIG. 2, a $4^{th}$ axis, containing a computer controlled rotation shaft, is added to an XYZ position system. This 4 axis fabrication system also has a materials delivery system mounted on the XYZ position system. In preferred embodiments, the materials delivery system is a polymer melt extrusion system which is able to directly deposit polymer material in a hot melt filament form, or a solution delivery system which can deliver viscous polymer solutions on to the computer controlled rotation shaft. The computer controlled rotation shaft driven by a server motor can be programmed precisely to rotation, stop and rotate back and forth at desired speeds. The rotating shaft can be equipped with a heating element or hosted in a temperature controlled environment to control the softness and viscosity of the delivered material so that the materials will exhibit the desired properties. For example, when using a polymer solution, the delivered materials can adhere better to each other and maintain a certain shape. The hot melt filament will bond to previously extruded filaments when they meet, therefore eliminating the need to use glue. For a given polymer, a set of preferred combinations of flow rate, head speed and melt chamber temperature can be established in order to produce sufficient adhesion between extrudate of adjacent layers at their cross-points while maintaining vertical channels between them, to provide interconnectivity throughout the entire structure.

The 3D tubular scaffolds may be fabricated using several methods, e.g., via a layer by layer fabrication technique or layer by layer assembling technique. In such an embodiment, each layer of 3D tubular scaffold is pre-fabricated using suitable polymer processing techniques according to the structure design.

The layers of the 3D tubular scaffold are then assembled together by putting several layers of the tubular scaffolds inside one another. Each layer of 3D tubular scaffold may have a different structure and may also be longer than the desired length of the final product. When the length of the construct is longer than the final desired product, the final product can be cut into the desired length using a mechanical device, such as a knife or a laser beam. One or more final 3D tubular scaffolds may be cut from a single assembled long construct.

Hot melt polymers may be used in the present invention for fabricating porous 3D tubular structures. Polymer pellets/particles/beads may be used directly without the need to fabricate polymeric filament first. To realize the direct use of polymer hot melt, the apparatus of the present invention has an extruder which is mounted on a dispensing arm. The extruder is equipped with a delivery mechanism, such as compressed air, a plunger, a extrusion screw, or a combination of the above, to force the molten polymer through a nozzle, which is attached to the extruder. The apparatus also comprises a rotary rod positioned underneath the nozzle. The extruded polymer thin filament deposits onto the rotating rotary rod according to a designed moving pathway in a layer by layer fashion. The rotary rod rotates to allow the polymer to deposit on surfaces of the rod while the extruder moves along the Y-axis, thereby forming a tubular shape, with polymer melt depositing in a desired pattern. Multiple layers of polymer melt can be deposited on the $4^{th}$ rotation axis to form a thicker wall with a porous structure. A porous structure thus can be obtained when the solidified polymer is removed from the rotation shaft. In order to allow for greater control over porosity, pore size and structure, either the dispensing arm, rotary rod or both move along a longitudinal axis. In addition to this longitudinal movement, the speed of the rotation of the rotary rod and the speed of the longitudinal movement of the dispensing arm and/or the rotary rod can also aid in the control of pore size tubular e of the 3D tubular scaffold.

In certain embodiments, the 3D scaffolds of the present invention may be manufactured using a 4-axis RP system, in which a dispensing device is mounted on the XYZ dispensing arm is used to dispense the polymer solution. The dispensing device is equipped with a delivery mechanism, such as compressed air, a plunger or a combination of the two, to force the polymer solution through a nozzle or a syringe needle which is attached to the dispensing device. The apparatus also comprises a rotary rod positioned underneath the nozzle. The extruded polymer solution stream deposits onto the rotating rotary rod in a layer by layer fashion. The rotary rod is equipped with a temperature control mechanism so that the polymer solution deposited onto the rotary rod is quickly solidified such as frozen, therefore, the deposited polymer solution can be kept at its deposited location and maintain certain size and shape. The freeze mechanism can be a temperature controlled freeze chamber or a rotary rod equipped with a cooling coil inside the shaft of the rod. Similar to the polymer melt deposition described above, the rotary rod rotates to allow the polymer solution to deposit on surfaces of the rod while the dispensing device moves along the Y-axies, thereby forming the 3D tubular scaffold with frozen polymer solution deposited in a particular pattern. Multiple layers of frozen polymer solution can be deposited on the $4^{th}$ rotation axis to form a thicker tubular wall porous structure. When finishing the deposition process, the frozen polymer structure, along with the rotary rod, is removed from the system and put into a freeze-drying chamber. The solvent of the polymer solution is then removed through a sublime process leaving behind a solid polymer structure. When finishing the solvent removing process, a porous tubular structure can be obtained when the dried polymer is removed from the rotary rod. In order to allow for greater control over porosity, pore size and structure, either the dispensing arm, rotary rod or both move along a longitudinal axis. In addition to this longitudinal movement, the speed of the rotation of the rotary rod and the speed of the longitudinal movement tubular of the dispensing arm and/or the rotary rod can also aid in the control of pore size of the 3D scaffold.

The present invention can use any type of thermal plastic polymer pellets, beads, particles, which are suitable for extrusion, injection molding, or forming solution with a solvent, as well as composites of two or more different thermal plastic polymer blends, inorganic particle/thermal plastic composites.

The materials used in this thermal extrusion apparatus can be a single type of thermal plastic polymer or a blend of two or more polymers in a preformed form. They can be a physical mixture of pellets/beads/particles of two or more thermoplastic polymers in a premixed mixture form. Additionally, the materials can be a physical mixture of inorganic particles and thermoplastic polymer particles/pellets/beads. Additionally, the materials can be a suspension inorganic particles suspended in a polymer solution. The materials can also be a solution from polymers and small molecules. In preferred embodiments, a micro single screw extruder is used, as it will result in a more homogeneous dispersion of inorganic particle in polymer matrix.

The material can also include a low molecular weight substance, such as a therapeutic agent.

In certain embodiments, the polymer melt extrusion mechanism or solution dispensing device is equipped with a on/off switch or a regulator which controls the extrusion rate of the polymer melt or solution. The switch can be a pressure regulator or a pressure valve that switch the compressed air on/off when compressed gas is used for extrusion of polymer melt. When the switch is on, the polymer melt or solution will be extruded though the nozzle tip by the air pressure inside the melt chamber. The switch can also be a electronic switch which turns on/off the motor that controls the rotation movement of the screw in a micro single-screw extruder or in a screw driven plunger.

The diameter of the extruded/dispensed polymer filament can be controlled by the inner diameter of the extrusion/dispensing nozzle and the extrusion/dispensing speed.

Applications of the 3D Tubular Scaffolds

The 3D tubular scaffolds of the present invention may be used, e.g., for regeneration of blood vessels. In one embodiment, the 3D tubular scaffold may be seeded and cultured with endothelia cells in vitro, and then implanted to replace the damaged blood vessel. In another embodiment, a small tubular scaffold may be seeded and cultured with endothelial cells, then inserted into a larger tubular scaffold witch has been seeded and cultured with smooth muscle cells. After co-culturing in vitro for certain period of time, the blood vessel construct then can be implanted to replace the damaged blood vessel.

The 3D tubular scaffolds of the present invention may be used as vascular stents, which when placed and expanded in a plagued and narrowed segment of a blood vessel, the stent will keep the blood vessel open for easy blood flow.

Additionally, the 3D tubular scaffolds of the present invention may be used, e.g., to fabricate porous tubular structure for large bone defect repair or bone tissue engineering, as trabecular bone is a tubular structure with bone marrow resides in the center portion of the tubular bone. With the porous wall structure, stem cells or osteoblasts may be seeded and culture to produced regenerated bone tissue.

The 3D tubular scaffolds of the present invention may be used as esophagus stents, which, when placed and expanded in a narrowed segment of a esophagus, will keep the esophagus open for easy food flow into stomach. Such an application will be advantageous for late stage esophagus cancer patients.

Similarly, the 3D tubular scaffolds of the present invention may also be used as stents designed for the intestines, the bile conduct, urinary tract, etc.

The 3D tubular scaffolds of the present invention may also be used, e.g., for nerve regeneration. The porous scaffolds can be used as periphery nerve conduit to guide the damaged nerve to regenerate. In this application, the two ends of the periphery nerve can be inserted into the 3D tubular structure and guide the nerve to grow and reunite.

What is claimed:

1. An apparatus for manufacturing a three-dimensional porous tubular scaffold, said apparatus comprising:
a base;
an XYZ position system connected to said base, wherein said XYZ position system provides a X-axis, a Y-axis and a Z-axis, thereby providing motions along said X-axis, said Y-axis and said Z-axis;
a material delivery system that is mounted upon and is moved by said XYZ position system along said X-axis, said Y-axis and said Z-axis;
a rotary rod driver connected to said base, said rotary rod driver being computer-controlled, wherein said rotary rod driver provides rotation around a rotational axis, wherein said rotational axis is parallel to said Y-axis, and wherein said rotary rod driver is programmed to rotate, stop and rotate back and forth at desired speeds;
a rod having an outside diameter, said rod being mounted in and rotatingly driven by said rotary rod driver, said rod being located underneath said material delivery system, and said rod being equipped with a freeze mechanism, wherein said freeze mechanism is a cooling coil inside said rod;
wherein said apparatus is controlled so as to directly deposit a continuous filament of said material to form a deposited filament in a pre-designed geometric pattern on said rod or on a previously deposited layer, as a result of motions of said material delivery system driven by said XYZ position system and said rod driven by said rotary rod driver, and thereby forming said three-dimensional porous tubular scaffold; and
wherein said three-dimensional porous tubular scaffold has an inside diameter that is substantially equal to said outside diameter of said rod.

2. The apparatus of claim 1, wherein a traveling speed along said X-axis, said Y-axis or said Z-axis is varied or a speed of said rotation of said rod around said rotational axis is varied so as to vary a diameter of said deposited filament.

3. The apparatus of claim 1, wherein a traveling speed along said X-axis, said Y-axis or said Z-axis is varied or a speed of said rotation of said rod around said rotational axis is varied so as to vary a porosity or a pore size of said three-dimensional porous tubular scaffold.

4. The apparatus of claim 1, wherein a later-deposited portion of said deposited filament crosses an earlier-deposited portion of said deposited filament at designed locations.

5. The apparatus of claim 1, wherein said deposited filament has a constant diameter.

6. The apparatus of claim 1, wherein said deposited filament has different diameters in different places.

7. The apparatus of claim 1, wherein said rod is equipped with a heating element.

8. The apparatus of claim 1, wherein said material delivery system comprises an extruder.

9. The apparatus of claim 1, wherein said material delivery system comprises an on/off switch or a pressure regulator that controls an extrusion rate of material from said material delivery system.

10. The apparatus of claim 1, wherein said material delivery system comprises a heater.

11. The apparatus of claim 1, wherein said material delivery system comprises a syringe.

12. The apparatus of claim 1, wherein said material delivery system comprises a pump.

13. The apparatus of claim 1, wherein said material delivery system contains a viscous solution.

14. The apparatus of claim 1, wherein said material delivery system contains a thermoplastic polymer.

15. The apparatus of claim 1, wherein said material delivery system contains a blend of two or more polymers in a preformed form or a physical mixture of pellets or beads or particles of two or more thermoplastic polymers in a premixed mixture form.

16. An apparatus for manufacturing a three-dimensional porous tubular scaffold, said apparatus comprising:
a base;
an XYZ position system connected to said base, wherein said XYZ position system provides a X-axis, a Y-axis and a Z-axis, thereby providing motions along said X-axis, said Y-axis and said Z-axis;
a material delivery system that is mounted upon and is moved by said XYZ position system along said X-axis, said Y-axis and said Z-axis;
a rotary rod driver connected to said base, said rotary rod driver being computer-controlled, wherein said rotary rod driver provides rotation around a rotational axis, wherein said rotational axis is parallel to said Y-axis, and wherein said rotary rod driver is programmed to rotate, stop and rotate back and forth at desired speeds;
a rod, said rod being mounted in and rotatingly driven by said rotary rod driver, said rod being located underneath said material delivery system, and said rod being equipped with a freeze mechanism, wherein said freeze mechanism is a cooling coil inside said rod;
wherein said apparatus is controlled so as to directly deposit a continuous filament of said material to form a deposited filament in a pre-designed geometric pattern on said rod or on a previously deposited layer, as a result of motions of said material delivery system driven by said XYZ position system and said rod driven by said rotary rod driver, and thereby forming said three-dimensional porous tubular scaffold; and
wherein during operation of said apparatus, said deposited filament changes its angular orientation with respect to an overall up-down direction of said apparatus.

17. An apparatus for manufacturing a three-dimensional porous tubular scaffold, said apparatus comprising:
a base;
an XYZ position system connected to said base, wherein said XYZ position system provides a X-axis, a Y-axis and a Z-axis, thereby providing motions along said X-axis, said Y-axis and said Z-axis;
a material delivery system that is mounted upon and is moved by said XYZ position system along said X-axis, said Y-axis and said Z-axis;
a rotary rod driver connected to said base, said rotary rod driver being computer-controlled, wherein said rotary rod driver provides rotation around a rotational axis, wherein said rotational axis is parallel to said Y-axis, and wherein said rotary rod driver is programmed to rotate, stop and rotate back and forth at desired speeds;
a rod, said rod being mounted in and rotatingly driven by said rotary rod driver, said rod being located underneath said material delivery system, and said rod being equipped with a freeze mechanism, wherein said freeze mechanism is a cooling coil inside said rod;
wherein said apparatus is controlled so as to directly deposit a continuous filament of said material to form a deposited filament in a pre-designed geometric pattern on said rod or on a previously deposited layer, as a result of motions of said material delivery system driven by said XYZ position system and said rod driven by said rotary rod driver, and thereby forming said three-dimensional porous tubular scaffold; and
wherein said material delivery system is a hot melt system and wherein rotation of said rod driver is controlled to draw said continuous filament exiting from said hot melt system so as to determine a diameter of said filament.

* * * * *